(12) United States Patent
Pomerantz et al.

(10) Patent No.: US 8,536,524 B2
(45) Date of Patent: Sep. 17, 2013

(54) FAST MUD GAS LOGGING USING TANDEM MASS SPECTROSCOPY

(75) Inventors: Andrew E. Pomerantz, Lexington, MA (US); Jerome Breviere, Taverny (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 184 days.

(21) Appl. No.: 13/267,576

(22) Filed: Oct. 6, 2011

(65) Prior Publication Data
US 2013/0087698 A1    Apr. 11, 2013

(51) Int. Cl.
*H01J 49/26*    (2006.01)

(52) U.S. Cl.
CPC ................................. *H01J 49/26* (2013.01)
USPC ........................... 250/296; 250/281; 250/282

(58) Field of Classification Search
USPC ................... 250/296, 297, 288, 281, 282
See application file for complete search history.

(56) References Cited

U.S. PATENT DOCUMENTS

| | | | |
|---|---|---|---|
| 4,635,735 A | 1/1987 | Crownover | |
| 2003/0062472 A1 | 4/2003 | Mullins et al. | |
| 2005/0082473 A1* | 4/2005 | Socki et al. | 250/288 |
| 2007/0169540 A1 | 7/2007 | Sterner et al. | |

FOREIGN PATENT DOCUMENTS

RU    2090912    9/1997

OTHER PUBLICATIONS

International Search Report and Written Opinion of PCT Application No. PCT/US2012/035820 dated Apr. 30, 2012: pp. 1-6.
Francis et al., "GeoVOC: A SIFT-MS method for the analysis of small linear hydrocarbons of relevance to oil exploration," International Journal of Mass spectrometry, 2007, vol. 268: pp. 38-46.
Hall et al., "Analysis of Borehole Gas with Direct Quadrupole Mass Spectrometry," AAPG Hedberg Conference, Jun. 2010: pp. 1-4.

* cited by examiner

*Primary Examiner* — Kiet T Nguyen
(74) *Attorney, Agent, or Firm* — Bridget Laffey; Rachel E. Greene; Jakub Michna

(57) ABSTRACT

Systems and methods for high speed mud gas logging are described. A general workflow of mud gas logging uses tandem mass spectroscopy. The workflow involves first separating the volatile components of the hydrocarbons (typically C8 and below) from the drilling fluid using a fluid extractor (or degaser). Extracted gases are then diluted in air and transported to an analyzer, which measures the concentration of each of those gases in air. A tandem mass spectroscopy-based analyzer is used that is able to quantify each of those hydrocarbon components, including resolving isomeric species, while tolerating the presence of the non-hydrocarbons. According to some embodiments, triple quadrapole mass spectroscopy is used.

29 Claims, 4 Drawing Sheets

FAST MUD GAS LOGGING USING TANDEM MASS SPECTROSCOPY

FIELD

This patent specification generally relates to mud gas logging while drilling. More particularly, this patent specification relates to the use of tandem mass spectroscopy for high-spatial resolution mud gas logging while drilling.

BACKGROUND

As a hydrocarbon wellbore is being drilled, hydrocarbons from the formation mix with the drilling fluid and are produced to surface. Mud gas or fluid logging is the practice of removing some of those hydrocarbons from the drilling fluid and measuring their concentration and composition. This practice can provide operators with their first measurement of the hydrocarbons present in the subsurface. Mud gas logging is performed commercially today by Schlumberger and several other companies. The primary analytical tool used to evaluate the hydrocarbons is a gas chromatograph. This technology is effective, but it has the disadvantage that the measurement time can be relatively slow. For example, a single analysis of hydrocarbons requires approximately one minute. For better depth resolution, it would be highly desirable to perform the analysis in a much shorter amount of time.

In the use of gas chromatography, gases are separated using a column and detected with a flame ionization detector or, in the case of Schlumberger's fluid logging service, with a mass spectrometer. The analysis time of about 1 minute is mainly due to the time required to separate the components using the gas chromatograph. Two techniques to accelerate the measurement by replacing the gas chromatograph have been described in the literature.

First is a technique called direct quadrapole mass spectrometry (DQMS), produced by Fluid Inclusion Technologies Inc. and described in a presentation titled "Analysis of Borehole Gas with Direct Quadrupole Mass Spectrometry" presented at the 2010 AAPG Hedberg Conference in Vail, Colo. (AAPG Search and Discovery Article #90110, Jun. 8-11, 2010). This method can be applied on gases liberated by crushing cuttings. In this technique, gases are analyzed using mass spectrometry without prior separation (i.e. without a gas chromatograph). Gases are ionized using electron ionization at 70 eV, a technique that causes analytes to break up into ionized fragments (a hard ionization technique). The resulting fragmentation pattern of each gas of interest is unique, in principle allowing each gas of interest to be quantified. However, the fragmentation patterns of the different gases are extremely similar, especially among isomers, meaning that implementation often requires unrealistically high signal-to-noise ratios and does not provide a proper differentiation between isomers of interest.

Second is a technique called selected ion flow-tube mass spectrometry (SIFT-MS). This instrument is described in *International Journal of Mass Spectrometry* 268 (2007) 38-46. In this technique, gases are analyzed using mass spectrometry without prior separation (i.e. without a gas chromatograph). Mass spectrometry alone can resolve the different alkanes, but it cannot resolve isomers. To distinguish isomers, the analysis is repeated using different ionization schemes, particularly using chemical ionization with different chemicals, some of which preferentially ionize branched over linear alkanes. A disadvantage of the technique is that these ionization schemes are quite complex (they involve termolecular reactions), meaning the results may not be robust enough but instead depend sensitively on the presence of various impurities. Additionally, the sensitivity for various hydrocarbon species can vary by orders of magnitude, requiring the analyte to be concentrated or diluted prior to analysis.

SUMMARY

According to some embodiments, methods and systems are described for analyzing gas contained in drilling mud brought to the surface as part of a wellbore drilling process. The method includes receiving a gaseous mixture including a plurality of gas components, the gaseous mixture having been separated from the drilling mud in which the mixture had been entrained; and performing tandem mass spectroscopy on the gaseous mixture resulting in a quantification of concentration of one or more of the gas components. According to some embodiments, the method is carried out during the wellbore drilling process.

According to some embodiments, the tandem mass spectroscopy comprises: a first mass spectroscopy process which isolates isomers having substantially the same molecular weight; a perturbation process following the first mass spectroscopy process which perturbs the isolated isomers; and a second mass spectroscopy process performed on the perturbed isomers which measures a mass distribution of the perturbed isomers. According to some embodiments, the first and second mass spectroscopy processes use quadrapole mass spectroscopy, and the perturbation processes uses collision-induced-dissociation to fragment the isomers.

According to some embodiments, the method includes a soft ionization process on the gaseous mixture performed prior to the first mass spectroscopy process, the soft ionization process being designed so as not to fragment a substantial amount of gas molecules in the gaseous mixture. The method can also include fitting the measured mass distribution of the perturbed isomers to a weighted linear combination of known patterns of molecules having the same molecular weight as the isolated isomers, the fitting resulting in a quantification of concentration of the isolated isomers.

According to some embodiments, the first mass spectroscopy process is performed using an ion trap associated with an external ionization source. The quantification of one or more of the gas components may not rely on a gas chromatography process.

According to some embodiments the method is performed in less than 30 seconds, and preferably is performed in less than 10 seconds. Even more preferably, the method is performed in less than one second.

As used herein, the term "tandem mass spectrometry," also known as MS/MS, $MS^2$ or $MS^n$, refers to mass spectrometry that involves multiple steps of mass spectrometry selection, with some form of fragmentation occurring in between the stages. As used herein the term "tandem mass spectrometry" includes mass spectrometry of any number of steps, which is sometimes referred to as $MS^n$, or "MS to the n." In general, a $MS^n$ process contains n mass spectrometry steps and n−1 perturbation steps.

As used herein the term "triple quadrupole mass spectrometry" refers to a type of tandem mass spectrometry in which two quadrupole mass spectrometers are used in series, with a quadrupole between them to act as a collision/transfer cell, for example to perform collision-induced dissociation.

BRIEF DESCRIPTION OF THE FIGURES

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

Figure 1:
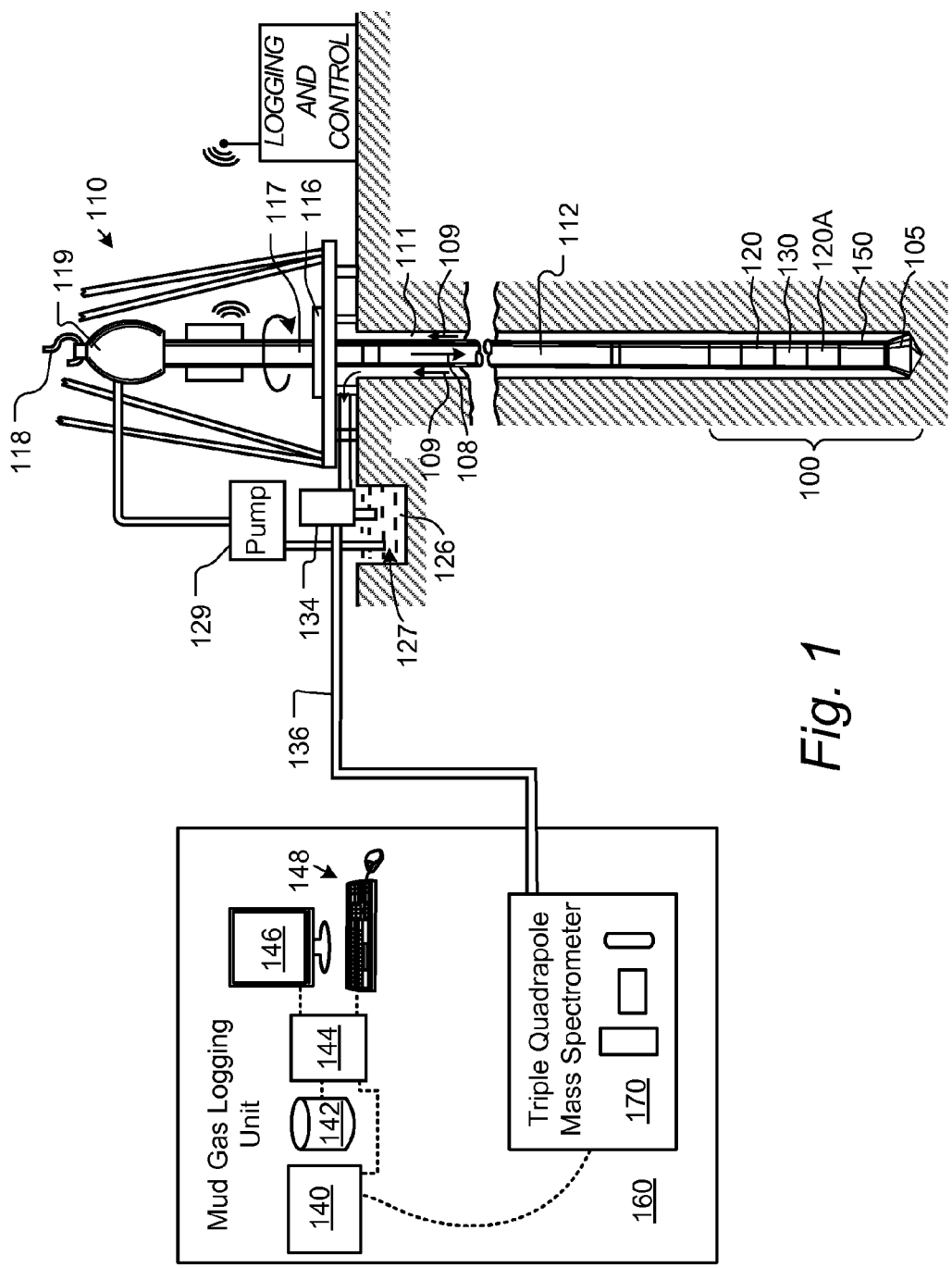
FIG. 1 illustrates an example of a wellbore drilling system including a mud gas logging unit, according to some embodiments.

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Specific details are given in the following description to provide a thorough understanding of the embodiments. However, it will be understood by one of ordinary skill in the art that the embodiments may be practiced without these specific details. For example, systems, processes, and other elements in the subject disclosure may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicate like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the subject disclosure may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to some embodiments, methods are described to perform mud gas or fluid logging significantly more quickly than current practice. For better depth resolution, it is highly desirable to perform the analysis in only a few seconds rather than about a minute. For example, at a drilling rate of 600 feet per hour, a one minute measurement interval as is common with gas chromatography-based mud gas logging corresponds to a depth resolution of 10 feet, while a measurement interval of six seconds, which is achievable using techniques described herein corresponds to a depth resolution of 1 foot.

According to some embodiments, a general workflow of mud gas logging using tandem mass spectroscopy is described. The workflow involves first separating the volatile components of the hydrocarbons (typically C8 and below) from the drilling fluid using a fluid extractor (or degaser). Extracted gases are then diluted in air and transported to an analyzer, which measures the concentration of each of those gases in air. According to some embodiments the extracted gases are not diluted in air (which under some circumstances can be advantageous). The concentration of each gas typically ranges from 1-500,000 ppm. Example gases of interest are the normal alkanes C1-C8, branched isomers of C4 and C5, aromatic species such as benzene, as well as non-hydrocarbons impurities such as alcohols and ammonia that may result from the drilling fluid. According to some embodiments, a tandem mass spectroscopy-based analyzer is used that is able to quantify each of those hydrocarbon components, including resolving isomeric species, while tolerating the presence of the non-hydrocarbons.

FIG. 1 illustrates an example of a wellsite drilling system including a mud gas logging unit with which the present invention can be employed, according to some embodiments. The wellsite can be onshore or offshore. In this exemplary system, a borehole 111 is formed in subsurface formations by rotary drilling in a manner that is well known. Embodiments of the invention can also use directional drilling, as will be described hereinafter.

A drill string 112 is suspended within the borehole 111 and has a bottom hole assembly 100 which includes a drill bit 105 at its lower end. The surface system includes platform and derrick assembly 110 positioned over the borehole 111, the assembly 110 including a rotary table 116, kelly 117, hook 118 and rotary swivel 119. The drill string 112 is rotated by the rotary table 16, energized by means not shown, which engages the kelly 117 at the upper end of the drill string. The drill string 112 is suspended from a hook 118, attached to a traveling block (also not shown), through the kelly 117 and a rotary swivel 119 which permits rotation of the drill string relative to the hook. As is well known, a top drive system could alternatively be used.

In the example of this embodiment, the surface system further includes drilling fluid or mud 126 stored in a pit 127 formed at the well site. A pump 129 delivers the drilling fluid 126 to the interior of the drill string 112 via a port in the swivel 119, causing the drilling fluid to flow downwardly through the drill string 112 as indicated by the directional arrow 108. The drilling fluid exits the drill string 112 via ports in the drill bit 105, and then circulates upwardly through the annulus region between the outside of the drill string and the wall of the borehole, as indicated by the directional arrows 109. In this well-known manner, the drilling fluid lubricates the drill bit 105 and carries formation cuttings up to the surface as it is returned to the pit 127 for recirculation. Before reaching the pit 127, the mud from the drillpipe passes through a gas separator/extractor 134 that is used to extract gas samples from the drilling mud for analysis by the mud gas logging unit 160.

The bottom hole assembly 100 of the illustrated embodiment a logging-while-drilling (LWD) module 120, a measuring-while-drilling (MWD) module 130, a roto-steerable system and motor, and drill bit 105.

The LWD module 120 is housed in a special type of drill collar, as is known in the art, and can contain one or a plurality of known types of logging tools. It will also be understood that more than one LWD and/or MWD module can be employed, e.g. as represented at 120A. (References, throughout, to a module at the position of 120 can alternatively mean a module at the position of 120A as well.) The LWD module includes capabilities for measuring, processing, and storing information, as well as for communicating with the surface equipment. In the present embodiment, the LWD module includes a fluid sampling device.

The MWD module 130 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, and an inclination measuring device.

Figure 2:
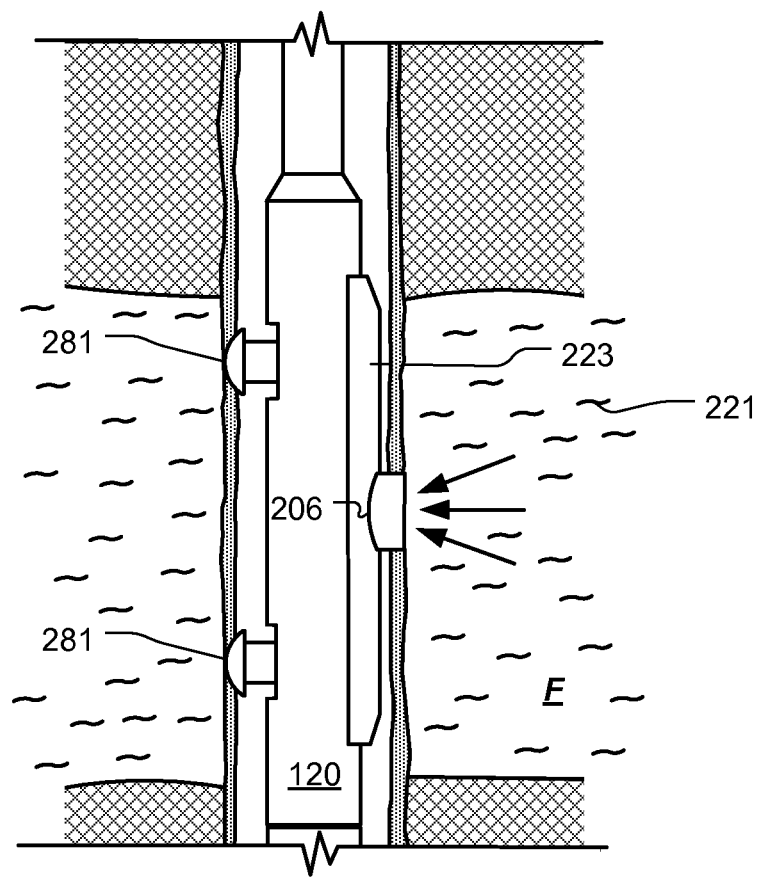
FIG. 2 depicts sampling-while-drilling logging device, as part of the LWD tool or tools shown in FIG. 1, according to some embodiments.

FIG. 2 is a simplified diagram of a sampling-while-drilling logging device of a type described in U.S. Pat. No. 7,114,562, incorporated herein by reference, utilized as the LWD tool 120 or part of an LWD tool suite 120A. The LWD tool 120 is provided with a probe 206 for establishing fluid communication with the formation and drawing the fluid 221 into the tool, as indicated by the arrows. The probe may be positioned in a stabilizer blade 223 of the LWD tool and extended therefrom to engage the borehole wall. The stabilizer blade 223 comprises one or more blades that are in contact with the borehole wall. Fluid drawn into the downhole tool using the probe 206 may be measured to determine, for example, pretest and/or pressure parameters. Additionally, the LWD tool 120 may be provided with devices, such as sample chambers, for collecting fluid samples for retrieval at the surface. Backup pistons 281 may also be provided to assist in applying force to push the drilling tool and/or probe against the borehole wall. Note that although FIG. 2 depicts a sampling-while-drilling logging device, according to some embodiments, the mud gas logging techniques described herein are employed in wells where there is no other type of measurement while drilling or logging while drilling being performed.

Referring again to FIG. 1, the extracted gases are diluted in air and transported to analyser 170 within mud gas logging unit 160. According to some embodiments, analyzer 170 is mounted directly to the degasser 134 such that no dilution and transport is necessary. Unit 160 includes one or more central processing units 140, storage system 144, communications and input/output modules 140, a user display 146 and a user input system 148. Input/output modules 140 include modules to communicate with and control analyzer 170.

Advantageously, analyser 170 performs a rapid analysis of the gas composition by eliminating the gas chromatograph and using exclusively a mass spectrometer. The analyser 170 exploits that fact that mass spectrometry is much faster than gas chromatography. Analyzer 170 employs tandem mass spectrometer that according to some embodiments is a triple quadrapole mass spectrometer. The triple quadrapole mass spectrometer consists of three quadrapoles in series. A quadrapole is an instrument that can separate ions based on their charge-to-mass ratio—i.e., a mass analyzer. The purpose of a having three quadrapoles is to perform a technique called tandem mass spectrometry. In tandem mass spectrometry, compounds are analyzed not only by measuring the charge-to-mass ratio distribution of charged particles produced when those compounds are ionized (which is the methodology in traditional mass spectrometry) but also by fragmenting those charged products and measuring the charge-to-mass ratios of the fragment products. This analysis of the fragmentation products provides additional information about the initial compounds, and in the subject disclosure this information is used to distinguish isomers.

Figure 3:
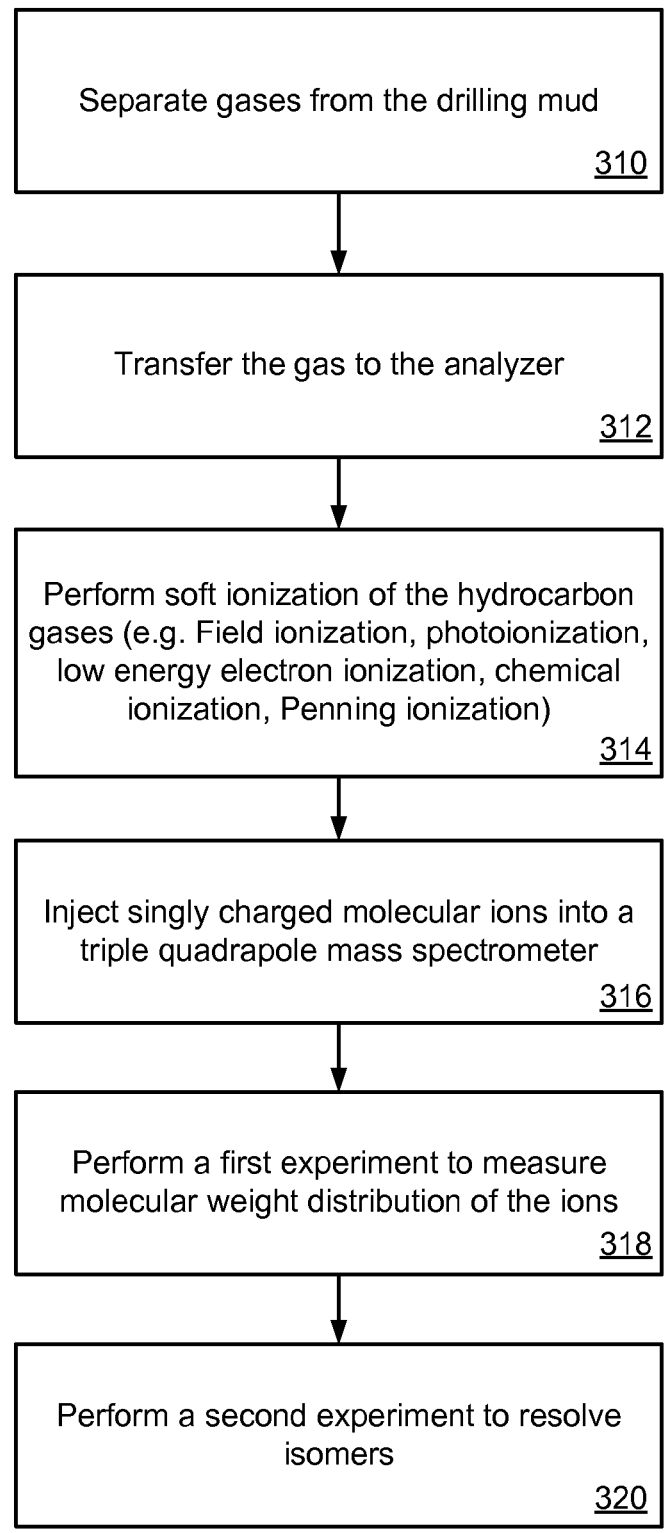
FIG. 3 is a flow chart illustrating steps in performing fast mud gas analysis using triple quadrapole mass spectrometry, according to some embodiments.

FIG. 3 is a flow chart illustrating steps in performing fast mud gas analysis using triple quadrapole mass spectrometry, according to some embodiments. In step 310, gases are separated from the drilling fluid. The drilling fluid comes to surface with entrained hydrocarbon gases from the subsurface formation (the goal is to study these gases). These gases have lower boiling points than the drilling fluid, so as an example the gases can be separated by heating the mixture. An example of a suitable separation procedures is the use of the Fluid Extractor (FLEX) operated by Schlumberger. According to some alternate embodiments, separation is performed by stirring the mixture.

In step 312, the gas is transferred to the analyzer. Gases liberated with the fluid extractor are mixed with air and pumped to the analyzer under partial vacuum through a plastic or metal tube (e.g. tube 136 in FIG. 1). Typically tube 136 is approximately 50 to 200 meters long. However, according to some embodiments the tube 136 is shortened considerably or eliminated altogether, by mounting the analyser 170 directly to the FLEX (or degasser) 134.

In step 314, a soft ionization of the hydrocarbon gases is performed. Gases must be ionized prior to mass spectrometric analysis. Conventionally, that analysis is performed using a hard ionization technique such as electron ionization at 70 eV. As used herein, hard ionization means than in addition to (or often instead of) placing a single electrical charge on a molecule, the molecule is broken up into several fragments, many of which obtain an electric charge. That technique is sufficient if the gases are previously separated (for example using a gas chromatograph), but it is typically insufficient without prior separation because many of the gases of interest here produce very similar fragmentation patterns. Instead, according to some embodiments, soft ionization is performed, in which (ideally) a single electron is removed from the molecule without creating any fragments; the resulting ion (consisting of the entire molecule as opposed to fragments) is referred to as a singly-charged molecular ion. Several different techniques, described below, can be used for producing singly-charged molecular ions from hydrocarbons, all of which result in positively-charged ions.

Field Ionization.

In this technique, molecules are placed in a large electric field (around $10^7$ V/cm) in a vacuum. This field is sufficient to remove one electron from a molecule. After removing the electron, this technique imparts essentially no additional internal energy to the molecules, creating essentially no fragments. This method produces singly-charged molecular ions of hydrocarbons.

Photoionization.

In this technique, analytes absorb light (typically a single photon in the vacuum ultraviolet range), and that photon energy is used to eject an electron. If the photon energy is just above the ionization potential, there will be little energy leftover for fragmentation, providing soft ionization.

Electron Ionization at Low Electron Energy.

Electron ionization is the most common ionization technique and consists of shooting an electron beam at the analyte. Some of the translational energy of the electrons is used to ionize the analytes. Typically 70 eV electrons are used, but that energy is much greater than typical ionization potentials (around 10 eV), and that excess energy typically leads to extensive fragmentation. Using low electron energy (around 15 eV) suppresses fragmentation, at the expense of reduced ionization efficiency.

Chemical Ionization.

In this technique, various gases are first ionized (typically using electron ionization), and those ionized gases are allowed to react with the analytes. Some of those reactions result in transferring an electrical charge to the analyte, resulting in ionized analytes. The efficiency of this process may vary greatly for different analytes (which could provide an important contrast mechanism), and often aggregates of the analyte and the ionization gas are formed (which can make analysis more complicated).

Penning Ionization.

In this technique, internally excited species chemically react with analytes, with that reaction using the internal energy to ionize the analyte. Penning ionization is a form of chemical ionization, and again this process can have greatly different efficiencies for different analytes, complicating the analysis but potentially providing valuable contrast.

It is noted that this soft ionization should be performed at low partial pressures of the analytes. If not, chemical reactions cannot occur resulting in a response that is not linear with the analyte concentration (in mass spectrometry this is called the matrix effect). That should not be a restriction for the ionization methods mentioned here; in fact field ionization and photoionization are routinely performed in vacuum. Additionally, according to some embodiments the analytes are jet-cooled with a molecular beam. This technique is characterized by intra-molecular vibrational supercooling due to collisions of sample molecules and carrier gas during the supersonic expansion. As the internal energy of the analytes is reduced, singly-charged molecular ions are preferably produced, leading to less fragmentation.

In step 316, the singly charged molecular ions are injected into a triple quadrupole mass spectrometer.

In step 318, a first experiment is performed to measure the molecular weight distribution of the ions. This can be accomplished easily by operating all the quadrupoles identically, such that the triple quadrupole mass spectrometer operates as a traditional single quadrupole mass spectrometer, and detecting the ions (which are now separated by mass) using a microchannel plate or other common detector. After this step, all of the species of interest are quantified except that isomers are not resolved. In the rare case where resolution of isomers is not required, the analysis is essentially complete. In the much more common case where resolution of isomers is required, that measurement is performed in the subsequent step. The advantage of this method of analysis over traditional gas chromatography (GC) is time: separation by mass can be accomplished in as little as 5 milliseconds per mass unit. According to some embodiments the heaviest molecule of interest in detecting is C8, with a mass of 114, which translates into a mass separation time of under one second. By comparison, typical separation by GC requires approximately 1 minute. Resolving isomers according to the subsequent steps adds to the measurement time, but the total measurement time is still considerably less than with the traditional GC.

In step 320, a second experiment is performed to resolve isomers. For example, two important isomers to resolve are nC4 (butane) and iC4 (isobutane). Both of these isomers have a nominal mass of 58 Da.

Figure 4:
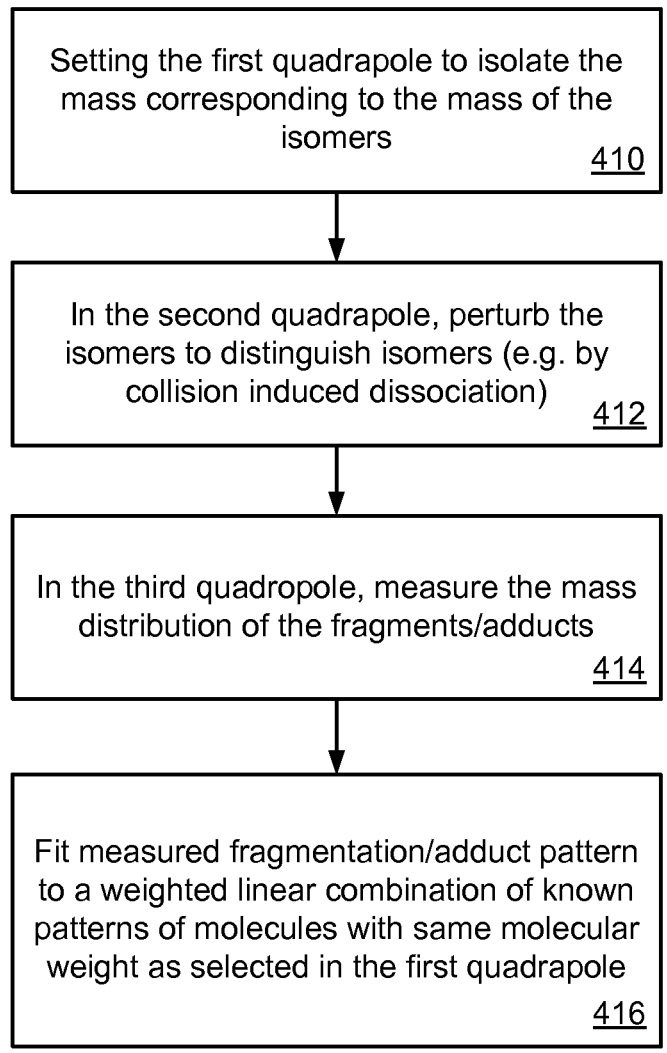
FIG. 4 is a flow chart illustrating further details in a second mass spectroscopy experiment to resolve isomers, according to some embodiments.

FIG. 4 is a flow chart illustrating further details in a second mass spectroscopy experiment to resolve isomers, according to some embodiments. In step 410, the first quadrupole is set to isolate the mass corresponding to the mass of the isomers (in the case of nC4 and iC4, that is 58 Da).

In step 412, the isomers are perturbed in the second quadrapole in such a way that distinct signals will result from the different isomers. One example of this perturbation is to fragment the isomers by collision induced dissociation, in which the ions are allowed to collide with uncharged gas atoms, resulting in fragmentation of the isomers; this process produces unique fragmentation patterns from different isomers. Another example of this perturbation is to create adducts of isomers using reagents that react specifically with one isomer but not the other; this process produces a high molecular weight adduct of one isomer without altering the other.

In step 414, the mass distribution of the fragments/adducts are measured in the third quadrupole.

In step 416, the measured fragmentation/adduct pattern of the isomers is fit to a weighted linear combination of the known fragmentation/adduct patterns of molecules with the same molecular weight as selected in the first quadrupole. In the case of adducts, the known patterns will depend on the identity of the reagent. The weighting coefficients from the fit represent the relative concentrations of the isomers.

It has been found that although the fragmentation patterns of isomers are often similar, they are not identical. It is difficult to quantify the concentration of each isomer when the signals from those isomers must be measured on top of a background of the signals from the other components in the mixture (as attempted in DQMS). Thus, according to some embodiments, the triple quadrupole system is used to simplify the mixture being fragmented. In this method of operation, only the isomers of interest pass through the first quadrupole, so there is no background coming from other ions. In other words, with techniques such as DQMS, the fragmentation patterns of all ~20 components are measured simultaneously, and because the fragmentation patters are so similar, it is difficult to quantify particular compounds; with the triple quadrupole mass spectrometer operated in this manner, only ~2 compounds (for example nC4 and iC4) rather than all ~20 compounds pass through the first quadrupole, resulting in a fragmentation pattern that is much simpler and can be analyzed at reasonable signal-to-noise levels. In addition, the signals from impurities (such as heavier hydrocarbons or mud additives) will be separated out of the basis of their different molecular weight—in favorable cases they will have a unique molecular weight and therefore can be identified and completely removed from the analysis, in unfavorable cases they will have the same molecular weight as a species of interest, in which case only the measurement of components at that molecular weight will be affected—making this analysis robust to contamination.

According to some embodiments, the instrument is constructed such that the first quadrupole is replaced with an ion trap associated with an external ionization source, with little change in the operation of the instrument, as is known to those skilled in the art. Similarly, according to some embodiments, the third quadrapole is replaced with an ion trap. According to some embodiments, the middle quadrapole is replaced with a hexapole or an octapole.

According to some embodiments, instead of an $MS^2$ arrangement in which mass spectrometry—perturbation—mass spectrometry, an $MS^3$ arrangement of tandem MS is used which includes mass spectrometry—perturbation—mass spectrometry—perturbation—mass spectrometry.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method of analyzing gas contained in drilling mud brought to the surface as part of a wellbore drilling process, the method comprising:
   receiving a gaseous mixture including a plurality of gas components, the gaseous mixture having been separated from the drilling mud in which the mixture had been entrained; and
   performing tandem mass spectroscopy on the gaseous mixture, the tandem mass spectroscopy resulting in a quantification of concentration of one or more of the gas components.

2. A method according to claim 1 wherein the method is carried out during the wellbore drilling process.

3. A method according to claim 1 wherein the tandem mass spectroscopy comprises:
   a first mass spectroscopy process which isolates isomers having substantially the same molecular weight;
   a perturbation process following the first mass spectroscopy process which perturbs the isolated isomers; and
   a second mass spectroscopy process performed on the perturbed isomers which measured a mass distribution of the perturbed isomers.

4. A method according to claim 3 wherein the first and second mass spectroscopy processes use quadrapole mass spectroscopy.

5. A method according to claim 4 wherein the perturbation processes includes using collision induced dissociation to fragment the isomers, and the second mass spectroscopy process measures the mass distribution of the fragments.

6. A method according to claim 3 further comprising performing a soft ionization process on the gaseous mixture prior to the first mass spectroscopy process, the soft ionization process designed so as not to fragment a substantial amount of gas molecules in the gaseous mixture.

7. A method according to claim 6 wherein the soft ionization process includes one or more techniques selected from a list comprising: field ionization, photoionization, low-energy electron ionization, chemical ionization, and penning ionization.

8. A method according to claim 3 wherein the tandem mass spectroscopy further comprises fitting the measured mass distribution of the perturbed isomers to a weighted linear combination of known patterns of molecules having the same molecular weight as the isolated isomers, the fitting resulting in a quantification of concentration of the isolated isomers.

9. A method according to claim 3 wherein the first mass spectroscopy process is performed using an ion trap associated with an external ionization source.

10. A method according to claim 3 wherein the third mass spectroscopy process is performed using an ion trap.

11. A method according to claim 3 further comprising:
    a second perturbation process following the second mass spectroscopy process; and
    a third mass spectroscopy process performed following the second perturbation process.

12. A method according to claim 1 wherein the wellbore is penetrating a subterranean hydrocarbon reservoir, and the identified gas components includes a plurality of hydrocarbon gas components having between one and eight carbon atoms per molecule.

13. A method according to claim 1 wherein the quantification of one or more of the gas components does not rely on a gas chromatography process, and includes quantification of concentrations of isomers.

14. A method according to claim 1 wherein the method is performed in less than 30 seconds.

15. A method according to claim 14 wherein the method is performed in less than 10 seconds.

16. A system for analyzing gas contained in drilling mud brought to the surface as part of a wellbore drilling process, the system comprising one or more instruments adapted to receive a gaseous mixture including a plurality of gas components, the gaseous mixture having been separated from the drilling mud in which the mixture had been entrained, and to perform tandem mass spectroscopy on the gaseous mixture resulting in a quantification of concentration of one or more of the gas components.

17. A system according to claim 16 wherein the one or more instruments adapted to perform tandem mass spectroscopy include:
    a first mass spectrometer adapted to isolate isomers having substantially the same molecular weight;
    a perturbation instrument, adapted to perturb the isolated using the first mass spectrometer; and
    a second mass spectrometer adapted to measured a mass distribution of the perturbed isomers.

18. A system according to claim 17 wherein the first and second mass spectrometers are quadrapole mass spectrometers.

19. A system according to claim 17 wherein the first and second mass spectrometers are ion trap mass spectrometers.

20. A system according to claim 17 wherein the first and second mass spectrometers are a combination of quadrapole mass spectrometers and ion trap mass spectrometers.

21. A system according to claim 18 wherein the perturbation instrument employs collision induced dissociation to fragment the isomers.

22. A system according to claim 18 wherein the perturbation instrument includes a quadrapole adapted to transfer fragments to the second mass spectrometer.

23. A system according to claim 18 wherein the perturbation instrument includes a hexapole adapted to transfer fragments to the second mass spectrometer.

24. A system according to claim 18 wherein the perturbation instrument includes an octapole adapted to transfer fragments to the second mass spectrometer.

25. A system according to claim 17 wherein the one or more instruments includes a soft ionizer adapted to ionize molecules in the gaseous mixture without substantial fragmentation prior to processing by the first mass spectrometer.

26. A system according to claim 17 further comprising a processing system adapted to fit a measured mass distribution of the perturbed isomers to a weighted linear combination of known patterns of molecules having the same molecular weight as the isolated isomers, thereby resulting in a quantification of concentration of the isolated isomers.

27. A system according to claim 16 wherein the one or more instruments are adapted to perform the tandem mass spectroscopy and quantification in less than 30 seconds.

28. A system according to claim 16 wherein the one or more instruments are adapted to perform the tandem mass spectroscopy and quantification in less than 10 seconds.

29. A system according to claim 16 wherein the quantification of one or more of the gas components does not rely on a gas chromatography process, includes quantification of concentrations of isomers.

\* \* \* \* \*